(12) United States Patent
Cabri et al.

(10) Patent No.: US 8,598,384 B2
(45) Date of Patent: Dec. 3, 2013

(54) CRYSTALLINE TEGLICAR

(75) Inventors: Walter Cabri, Rozzano (IT); Mauro Marzi, Rome (IT); Fabrizio Giorgi, Ardea (IT); Emanuela Tassoni, Ciampino (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 589 days.

(21) Appl. No.: 12/672,099

(22) PCT Filed: Jul. 31, 2008

(86) PCT No.: PCT/EP2008/060099
§ 371 (c)(1),
(2), (4) Date: Feb. 23, 2011

(87) PCT Pub. No.: WO2009/019199
PCT Pub. Date: Feb. 12, 2009

(65) Prior Publication Data
US 2011/0136905 A1    Jun. 9, 2011

(30) Foreign Application Priority Data
Aug. 7, 2007   (EP) ..................................... 07113904

(51) Int. Cl.
*C07C 229/00* (2006.01)
*A01N 33/02* (2006.01)

(52) U.S. Cl.
USPC .......................................... 562/561; 514/663

(58) Field of Classification Search
None
See application file for complete search history.

(56) References Cited

FOREIGN PATENT DOCUMENTS

| WO | 99/59957 | * 11/1999 |
|---|---|---|
| WO | 99/59957 | 6/2002 |

OTHER PUBLICATIONS

Giannessi, F. et al.. "Discovery of a Long-Chain Carbamoyl Aminocarnitine Derivative, a Reversible Carnitine Palmitoyltransferase Inhibitor with Antiketotic and Antidiabetic Activity" Journal of Medicinal Chemistry, vol. 46, No. 2, 2003, pp. 303-309.

* cited by examiner

Primary Examiner — Paul A Zucker
Assistant Examiner — Mark Luderer
(74) Attorney, Agent, or Firm — Lucas & Mercanti, LLP

(57) ABSTRACT

The present invention relates to a new crystalline form of R-4-trimethylammonium-3-(tetradecylcarbamoyl)-amino butyrate (also named crystalline Form I of ST 1326 or teglicar), a process for its preparation and pharmaceutical compositions containing same.

6 Claims, 3 Drawing Sheets

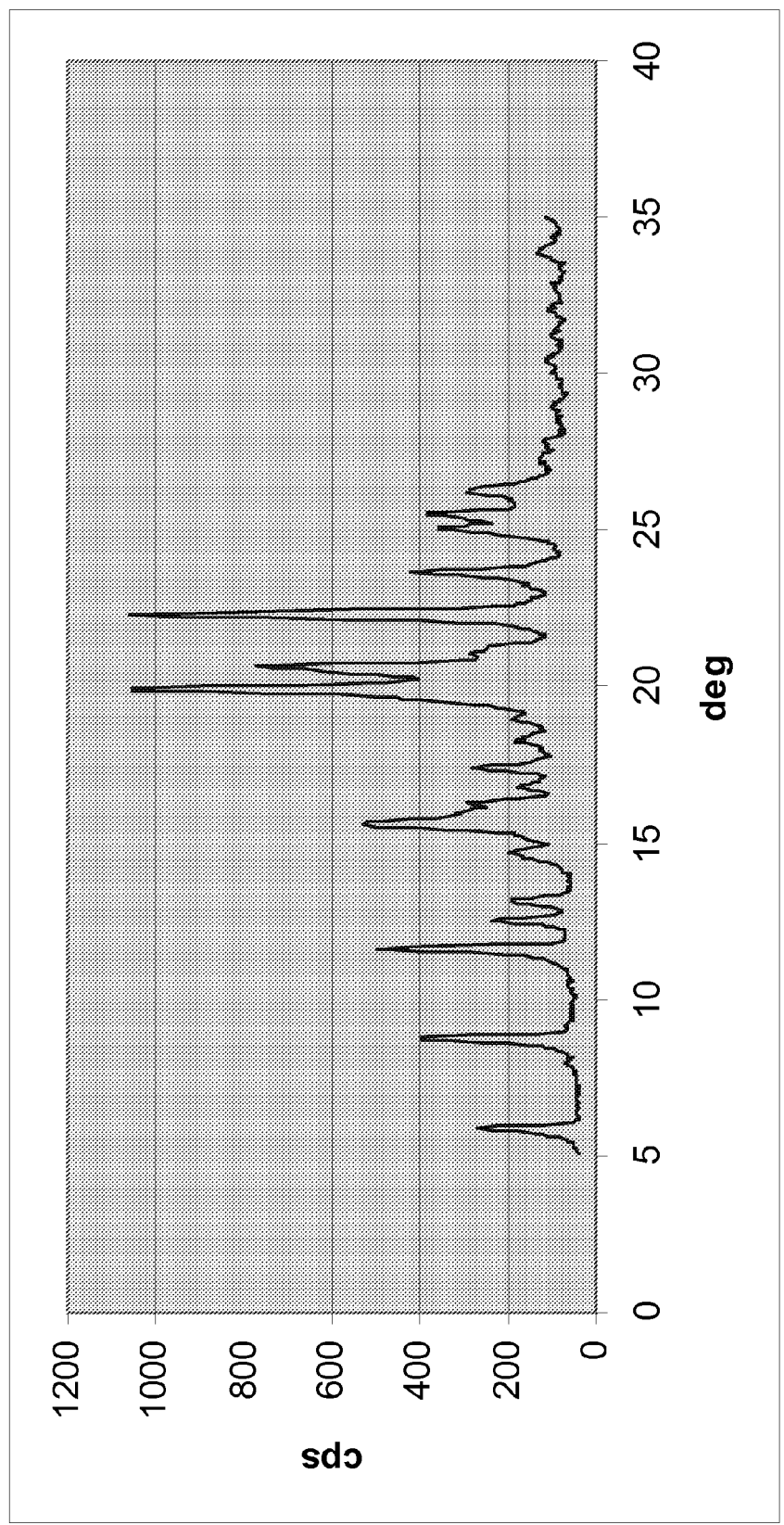
Figure 1: X-ray powder diffractogram of crystalline Form I teglicar

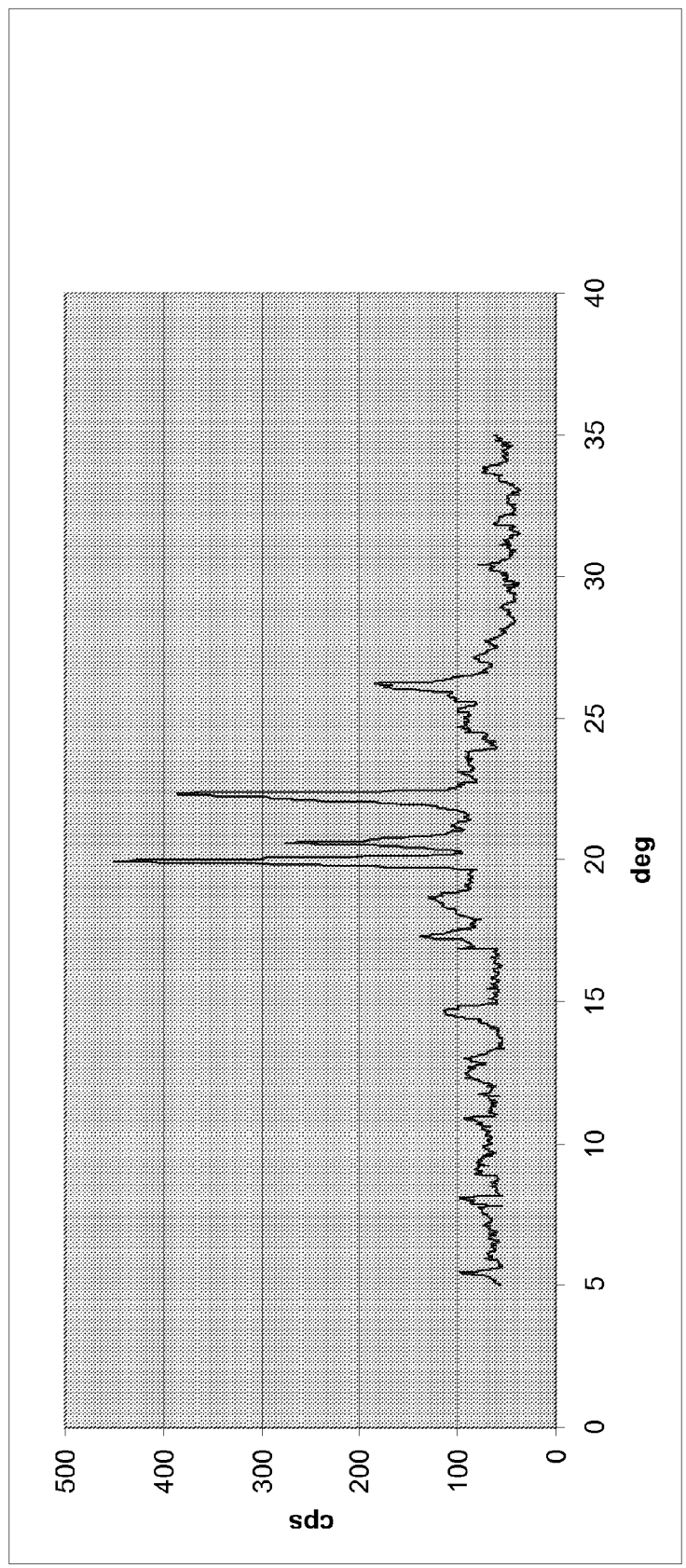
Figure 2: X-ray powder diffractogram of teglicar preparation as reported in WO99/59957

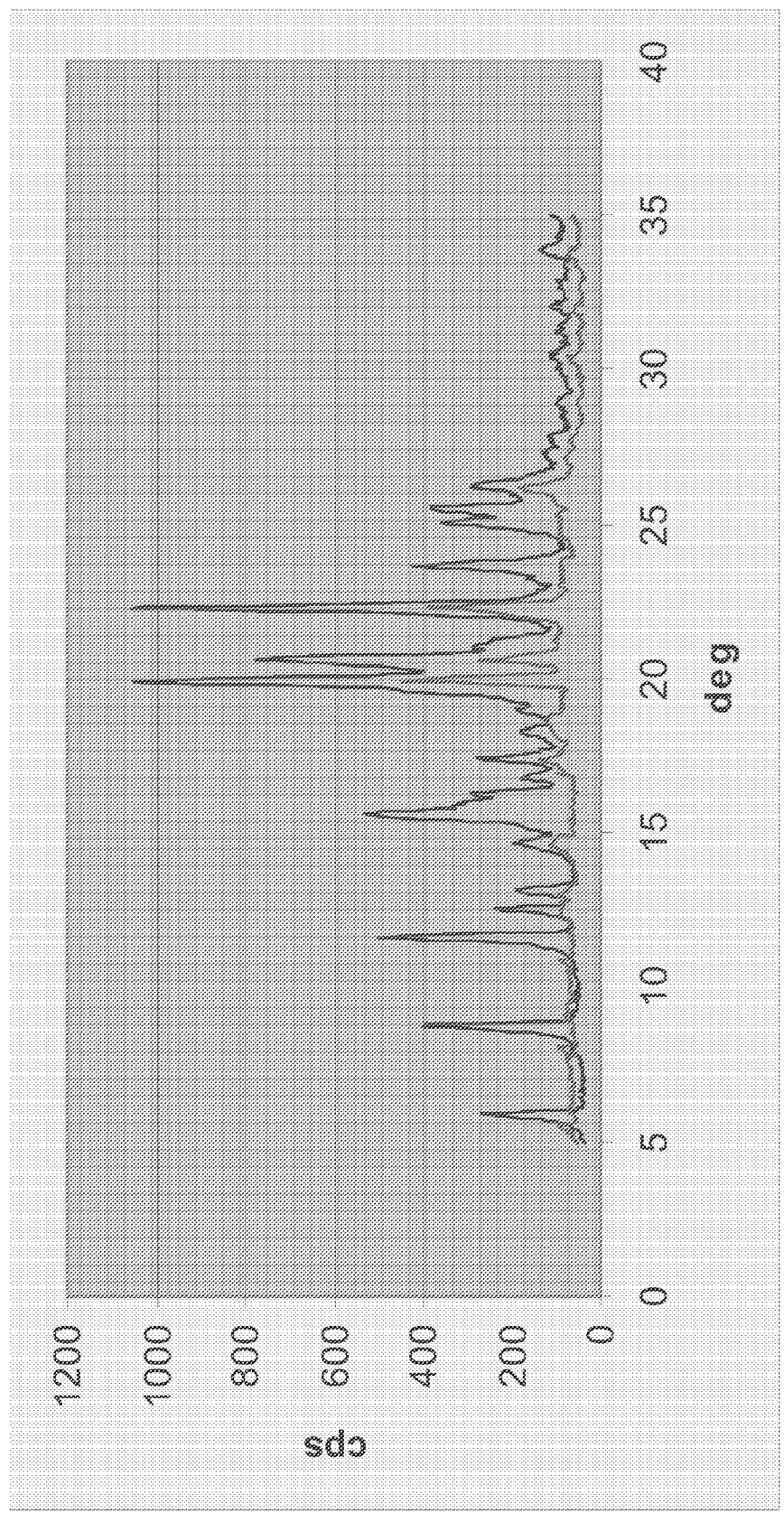
Figure 3: Comparison of diffractograms of Figure 1 and Figure 2

CRYSTALLINE TEGLICAR

This application is a 35 U.S.C. §371 national phase of PCT/EP2008/060099 filed on Jul. 31, 2008, which claims priority to and the benefit of European Application No. 07113904.2 filed on Aug. 7, 2007, the contents of which are incorporated herein by reference.

FIELD OF THE INVENTION

The present invention relates to a new crystalline form of R-4-trimethylammonium-3-(tetradecylcarbamoyl)-amino butyrate (also named ST1326 or teglicar), a process for its preparation and pharmaceutical compositions containing same.

BACKGROUND OF THE INVENTION

International patent application WO 99/59957 and J. Med. Chem. 2003, 46, 303-309 describe the synthesis of some new compounds having inhibiting activity against carnitine palmitoyl transferase (CPT).

Among the compounds synthesized and tested one of the most interesting is R-4-trimethylammonium-3-(tetradecyl-carbamoyl)-amino butyrate (also named ST 1326 or teglicar [INN]), whose synthesis is reported in Example 15 of WO 99/59957, and which corresponds to compound 17 of J. Med. Chem. 2003, 46, 303-309.

This compound was described as an agent able to selectively inhibit in vitro L-CPT I (liver CPT isoform I) with respect to M-CPT I (muscle CPT isoform I) and to depress ketogenesis in vivo (fasted rats). It also showed a good reduction of serum glucose levels in a diabetic mouse model, without any significant change in heart weight and triglycerides content. Owing to its encouraging activity and pharmacological profile, this compound was selected as a candidate for clinical development as an antiketotic and antidiabetic drug.

WO 2005/077354 discloses the use of the same compound for the preparation of an anti-tumour medicament.

However neither of these references indicate whether this compound is obtained in an amorphous or in a crystalline state.

Repetition of the preparation methods reported in these two references (WO 99/59957 and J. Med. Chem. 2003, 46, 303-309) has now allowed to establish that this compound was obtained as a mixture of a crystalline and an amorphous form.

X ray powder diffraction is the most widely used technique in the identification and characterisation of crystalline solids, each of which produces a distinctive diffraction pattern. Both the positions and the relative intensity of the lines are indicative of a particular phase and material, providing a "fingerprint" for comparison.

In contrast to a crystalline pattern consisting of a series of sharp peaks, amorphous materials (liquids, glasses etc.) produce a broad background signal. Powder X ray diffraction can be used to determine the crystallinity of the different preparations of the same product.

Many drugs, old and new, were discovered and rushed into market as their 'suitable' crystalline forms and had never been screened thoroughly for their potential polymorphic forms. With the recent technological advancement of solid state chemistry, it is possible that new polymorphic forms can be discovered, which have never been seen before.

The new polymorphic forms are often able to deliver therapeutic advantages and represent one of the new challenges of the pharmaceutical industry. As a matter of fact polymorphism, the ability of a molecule to crystallize into more than one crystal arrangement, can have a profound effect on the shelf life, solubility, formulation properties, and processing properties of a drug.

More importantly, the action of a drug can be affected by the polymorphism of the drug molecules. Different polymorphs can have different rates of uptake in the body, leading to lower or higher biological activity than desired. In extreme cases, an undesired polymorph can even be toxic. The occurrence of an unknown polymorphic form during manufacture can have an enormous impact on a drug company.

Therefore it is vital that researchers involved in the formulation of crystalline products be able to select the polymorph with the correct properties and anticipate problems such as the unwanted crystallization of other polymorphs.

Surprisingly, a very large number of pharmaceuticals exhibit the phenomenon of polymorphism. 70% of barbiturates, 60% of sulfonamides and 23% of steroids exist in different polymorphic forms.

Conducting a crystallization study on teglicar led to the claimed invention.

DESCRIPTION OF THE INVENTION

The main object of the present invention is to provide a new crystalline form of R-4-trimethylammonium-3-(tetradecyl-carbamoyl)-amino butyrate (also named ST 1326 or teglicar [INN]), also named crystalline Form I of teglicar.

The new crystalline Form I of teglicar is characterized by the physical-chemical parameters provided in the description.

In particular such parameters are selected from the group comprising:

the X ray diffraction spectra;

the DSC data (Differential Scanning Calorimetry); and the Fourier Transform InfraRed (FTIR) spectra.

FIG. 1 shows the X-ray powder diffractogram of crystalline Form I of teglicar.

The characteristic diffraction peaks are given on the following table:

| Degrees 2-Theta ± 0.2 | Relative intensity (%) |
|---|---|
| 5.90 | 25 |
| 8.80 | 37 |
| 11.65 | 47 |
| 12.55 | 22 |
| 13.20 | 18 |
| 14.70 | 18 |
| 15.60 | 50 |
| 17.45 | 26 |
| 19.95 | 99 |
| 20.65 | 73 |
| 22.30 | 100 |
| 23.65 | 40 |
| 25.10 | 34 |
| 25.55 | 36 |
| 26.30 | 27 |
| 33.85 | 13 |

The most representative peaks are:

| Degrees 2-Theta ± 0.2 | Relative intensity (%) |
| --- | --- |
| 11.65 | 47 |
| 15.60 | 50 |
| 19.95 | 99 |
| 20.65 | 73 |
| 22.30 | 100 |
| 23.65 | 40 |
| 25.10 | 34 |
| 25.55 | 36 |
| 26.30 | 27 |

The FT-IR spectrum (in KBR) of crystalline Form I of teglicar has also been provided. In the following table main signals ($cm^{-1}$) characteristic of this crystalline form are reported:

| Frequency (cm−1) | Intenisty (% T) |
| --- | --- |
| 3253.2 | 56 |
| 3031.2 | 60 |
| 2951.3 | 55 |
| 2918.9 | 36 |
| 2848.9 | 41 |
| 1668.9 | 43 |
| 1600.4 | 38 |
| 1561.1 | 41 |
| 1469.7 | 47 |
| 1445.8 | 60 |
| 1418.1 | 56 |
| 1390.3 | 44 |
| 1324.3 | 59 |
| 1265.8 | 55 |
| 1197.4 | 70 |
| 1138.5 | 77 |
| 1089.0 | 76 |
| 1070.4 | 75 |
| 969.6 | 70 |
| 933.7 | 58 |
| 901.5 | 77 |
| 870.9 | 76 |
| 808.2 | 80 |
| 720.0 | 55 |
| 501.0 | 76 |

The main advantages of this new crystalline form are the following:
I. it is obtained as pure compound and therefore no purification steps are needed, before proceeding to its isolation/separation from the crystallization medium/solvent;
II. increased hygroscopic stability, i.e. the water content is not subject to changes with time; the increased hygroscopic stability of Form I of teglicar with respect to the mixture obtainable as described in WO 99/59957 has been shown by a KF (Karl Fisher) analysis (see Example 4).
III. this increased stability renders the compound more manageable during the isolation steps, especially filtration procedures; and
IV. this increased stability also renders easier to formulate the compound in the final pharmaceutical composition.

Another object of the present invention is a process for the preparation of the above crystalline form.

The crystalline Form I of teglicar is prepared according to the following procedure:
a) to a solution of (R)-aminocarnitine in methanol tetrabutylammonium chloride and tetradecylisocyanate are added under stirring at low temperature (from 2 to 10° C.); tetradecylisocyanate is added slowly; after the addition, the solution become a suspension;
b) the suspension is filtered and the organic solvent is concentrated under vacuum;
c) to the viscous oil so obtained acetonitrile is added and stirred overnight to give a solid;
d) the solid is separated by filtration, washed with acetonitrile, dissolved in water and filtered;
e) the solution so obtained is dropped into a flask containing acetonitrile under stirring, giving at first a suspension, but after some (2 to 5) days at low temperature (from 2 to 10° C.) a white solid product is obtained with a high yield (90%);
f) the solid is isolated from the solvent according to normal/standard procedures.

All the above steps are common steps of crystallization that can be carried out by a normal chemistry practitioner, either on a lab scale or in industrial scale, just selecting the proper conditions, such volumes, temperatures and times.

Crystalline form I of teglicar has an inhibiting activity against carnitine palmitoyl transferase (CPT). This biological activity renders it useful for the preparation of medicament for the treatment and/or prevention of hyperglycaemia, diabetes and disorders related thereto, such as for example diabetic retinopathy, diabetic neuropathy and obesity.

The crystalline Form I of teglicar of the present invention is also useful as active ingredient for the treatment and/or prevention of cardiovascular disorders, such congestive heart failure. Moreover, the crystalline Form I of teglicar of the present invention is also useful as active ingredient for the treatment and/or prevention of ketonic states, wherein it is intended that the pathological disorder is characterized by high levels of ketonic bodies in the body. Moreover the use of the crystalline Form I for the treatment of tumors is also an object of the present invention.

A further object of the present invention is a pharmaceutical composition containing the crystalline Form I of teglicar.

The compositions of the present invention are conventional and are obtained with methods commonly used in the pharmaceutical industry. According to the desired administration route shall be in solid or liquid form, suitable to the oral, parenteral, intravenous, intranasal or transdermal route.

The dose of the active ingredient (crystalline Form I of teglicar of the present invention) will vary depending on the administration route, the grade of the pathology top be treated and the general conditions of the subject to be treated.

The dosage and administration schedule will be determined by the clinical expert or the physician. Generally a therapeutic effect can be obtained at dosages varying from 1 to 100 mg/kg body weight.

A further object of the present invention is the process for the preparation of the pharmaceutical composition of the invention comprising admixing crystalline Form I of teglicar of the present invention crystalline Form I of teglicar of the present invention with pharmaceutically acceptable excipients and/or vehicles.

The invention will be illustrated in detail in the following Examples, which make reference to the following Figures.

DESCRIPTION OF FIGURES

FIG. 1 shows the X-ray powder diffractogram of crystalline Form I of teglicar (according to Example 1).

FIG. 2 shows the X-ray powder diffractogram of teglicar prepared as reported in WO99/59957 (according to Comparative Example 2).

FIG. 3 shows the comparison of the two diffractograms of FIG. 1 and FIG. 2, where the black line (/) is the diffractogram of the crystalline Form I of teglicar and the grey line (/) is the X-ray powder diffractogram of teglicar prepared as reported in WO99/59957.

EXAMPLES

Example 1

Preparation of Crystalline Teqlicar

To a solution of (R)-aminocarnitine (22.0 g, 137.5 mmol) in MeOH (120 mL), tetrabutylammonium chloride (200 mg) and, slowly, tetradecylisocyanate (44 mL, 38.23 g, 160 mmol) were added under stirring keeping the temperature at 5° C. (tetradecylisocyanate was added in about 1.5 h; once added the first 10 mL, the solution became a suspension). Then MeOH (120 mL) was added and the mixture was stirred at room temperature (RT).

The suspension was filtered and the organic solvent was concentrated under vacuum. To the viscous oil acetonitrile (200 mL) was added and stirred overnight to give a solid. Solid was separated by filtration, washed with acetonitrile dissolved in distilled water (50 mL) and filtered on Celite.

The solution was dropped into a flask containing acetonitrile (700 mL) under stirring, giving at first a suspension but after 5 days at 5° C., 45 g of white solid of product was obtained (yield=90%).

HPLC: Column Spherisorb S5 SCX 4.6×250 mm, eluent A: 60% Phosphate buffered ($KH_2PO_4$) 50 mM, pH 3.7, eluent B: 40% Acetonitrile, Flow-rate: 1 ml/ml, 205 nm, column temperature 30° C., Rt 9.6 min, strength 95%. ESI-MS ($M+H^+$) 400.

Solid State Characterization of Crystalline Form I of Teglicar
X-Ray Powder Diffractrometry The X-ray powder diffractogram on about 15 mg of ground powder was obtained using a computer controlled XRD powder diffraction apparatus and examined under inert atmosphere.

The tube conditions were 40 KV×40 mA CuKα, the windows used were aperture 0.3°, and closing 0.15°. The time for each step scan was 7 s, the 2-θ range was 5°-35°.

After the acquisition, an accurate analysis of the spectrum was performed adopting a procedure for the peak evaluation taking into account both the minimum peak width and an estimated amount of the disordered part. It is concluded that sample is crystalline.

FIG. 1 shows the X-ray powder diffractogram of crystalline Form I of teglicar.

The characteristic main diffraction peaks are given on the following table:

| Degrees 2-Theta ± 0.2 | Relative intensity (%) |
|---|---|
| 5.90 | 25 |
| 8.80 | 37 |
| 11.65 | 47 |
| 12.55 | 22 |
| 13.20 | 18 |
| 14.70 | 18 |
| 15.60 | 50 |
| 17.45 | 26 |
| 19.95 | 99 |
| 20.65 | 73 |
| 22.30 | 100 |
| 23.65 | 40 |
| 25.10 | 34 |
| 25.55 | 36 |
| 26.30 | 27 |
| 33.85 | 13 |

The most representative peaks are:

| Degrees 2-Theta ± 0.2 | Relative intensity (%) |
|---|---|
| 11.65 | 47 |
| 15.60 | 50 |
| 19.95 | 99 |
| 20.65 | 73 |
| 22.30 | 100 |
| 23.65 | 40 |
| 25.10 | 34 |
| 25.55 | 36 |
| 26.30 | 27 |

FT-IR Spectrum

The diffuse reflectance FT-IR spectrum of crystalline Form I of teglicar were collected on a 2% sample in KBr with a Thermo Nicolet 5700 spectrometer.

The FT-IR spectrum (in KBR) of crystalline Form I of teglicar was also provided. In the following table main signals ($cm^{-1}$) characteristic of this crystalline form are reported:

| Frequency (cm-1) | Intenisty (% T) |
|---|---|
| 3253.2 | 56 |
| 3031.2 | 60 |
| 2951.3 | 55 |
| 2918.9 | 36 |
| 2848.9 | 41 |
| 1668.9 | 43 |
| 1600.4 | 38 |
| 1561.1 | 41 |
| 1469.7 | 47 |
| 1445.8 | 60 |
| 1418.1 | 56 |
| 1390.3 | 44 |
| 1324.3 | 59 |
| 1265.8 | 55 |
| 1197.4 | 70 |
| 1138.5 | 77 |
| 1089.0 | 76 |
| 1070.4 | 75 |
| 969.6 | 70 |
| 933.7 | 58 |
| 901.5 | 77 |
| 870.9 | 76 |
| 808.2 | 80 |
| 720.0 | 55 |
| 501.0 | 76 |

Comparative Example 2

Preparation of Teqlicar as Reported in WO99/59957

Example 15 of WO99/59957 was repeated to give 750 mg of product.

The product so obtained was characterized by using the procedures, methods and apparatuses described before in connection with crystalline Form I of teglicar. The peaks evaluation taking into account the minimum peak width, highlights only a mixture of a crystalline and an amorphous form.

FIG. 2 shows the X-ray powder diffractogram of the teglicar preparation as reported in WO99/59957. By evaluation of the whole diffractogram, it was concluded that only few peaks of the crystalline form were present (those with highest relative intensity), as reported in the following table and as evident also from the comparison of the two diffractograms reported in FIG. 3.

| Degrees 2-Theta ± 0.2 | Relative intensity (%) |
|---|---|
| 19.95 | 100 |
| 20.60 | 61 |
| 22.35 | 86 |
| 26.20 | 41 |

The other peaks representative of crystalline Form I at Degrees 2-Theta 11.65, 15.60, 23.65, 25.10 and 25.55 are not visible, as they are covered under the background signal. This proves that the compound under examination was a mixture of a crystalline and an amorphous form.

Comparative Example 3

Preparation of Teglicar as Amorphous

Example 1 and Comparative Example 2 were repeated and the solids so obtained were dissolved in 6 ml of water. The solutions were each separated in 6 parts, fast frozen with a freeze-dryer and lyophilized.

The lyophilization conditions were as follows:
Thermal treatment: −40° C. 180 min.
Drying phase: −40° C. 180 min. 100 mT
−10° C. 360 min. "

The solids obtained were characterized by using the procedures, methods and apparatuses described before in connection with crystalline Form I of teglicar and allowed to conclude that both products were amorphous compounds, characterized by physico-chemical properties different from those of the crystalline form prepared according to Example 1.

Solid State Characterization of Amorphous Teglicar
X-Ray Powder Diffractrometry

After the acquisition, an accurate analysis of the spectrum was performed adopting a procedure for the peak evaluation taking into account both the minimum peak width and an estimated amount of the disordered part. It is concluded that both samples obtained according to Comparative Examples 3 were amorphous compounds.

FT-IR Spectrum

In the following table main signals ($cm^{-1}$) characteristic of these amorphous forms obtained according to Comparative Example 3 are reported:

| Frequency ($cm^{-1}$) | Intensity (% T) |
|---|---|
| 3284.6 | 47 |
| 3031.6 | 53 |
| 2917.5 | 36 |
| 2849.6 | 39 |
| 1658.5 | 44 |
| 1583.5 | 37 |
| 1468.1 | 45 |
| 1390 | 43 |
| 1317.8 | 52 |
| 1274 | 50 |
| 1133.8 | 68 |
| 1087 | 66 |
| 971.5 | 64 |
| 973.6 | 57 |
| 901.9 | 65 |
| 875.3 | 66 |
| 720.9 | 52 |

Example 4

Karl Fisher Analysis (Water Content)

Water content analysis were carried out with a Metrohm's KF Coulometer, using Metrohm glass vials (volume 10 mL) with elastometric tight closure, with about 10÷40 mg of sample. The samples were analyzed at 140° C.

The reference was an empty vial of the same kind. Sodium Tartrate diHydrate (theoretical amount is 15.66%) was used to assess the calibration of the apparatus with regard to the humidity.

The initial water content determined for compounds of Example 1 and Comparative Example 2 was (t=0) about 4.8%. Then these compounds were kept at room temperature under the same conditions, exposed to the air for 18 hours. A KF analysis was repeated on both samples and the results showed a large increase of $H_2O$ content for compound of Comparative Example 2.

| Compound | KF (% $H_2O$) t = 0 | KF (% $H_2O$) t = 18 h |
|---|---|---|
| Example 1 | 4.8% | 5.8% |
| Comparative Example 2 | 4.9% | 15.2% |

Moreover the Form I of teglicar (Example 1) remains very manageable.

The invention claimed is:

1. Crystalline Form I of R-4-trimethylammonium-3-(tetradecylcarbamoyl)-amino butyrate.

2. The crystalline Form I according to claim 1, which shows an X-ray powder diffraction pattern comprising the following characteristic peaks expressed in degrees 2θ±0.2:

| Degrees 2-Theta ± 0.2 | Relative intensity (%) |
|---|---|
| 11.65 | 47 |
| 15.60 | 50 |
| 19.95 | 99 |
| 20.65 | 73 |
| 22.30 | 100 |
| 23.65 | 40 |
| 25.10 | 34 |
| 25.55 | 36 |
| 26.30 | 27. |

3. The crystalline Form I according to claim 1, which shows an X-ray powder diffraction pattern comprising the following characteristic peaks expressed in degrees 2θ±0.2:

| Degrees 2-Theta ± 0.2 | Relative intensity (%) |
|---|---|
| 5.90 | 25 |
| 8.80 | 37 |
| 11.65 | 47 |
| 12.55 | 22 |
| 15.60 | 50 |
| 17.45 | 26 |
| 19.95 | 99 |
| 20.65 | 73 |
| 22.30 | 100 |
| 23.65 | 40 |
| 25.10 | 34 |
| 25.55 | 36 |
| 26.30 | 27. |

4. The crystalline Form I according to claim 1, which shows an X-ray powder diffraction pattern having the following characteristic peaks expressed in degrees 2Θ±0.2:

| Degrees 2-Theta ± 0.2 | Relative intensity (%) |
|---|---|
| 5.90 | 25 |
| 8.80 | 37 |
| 11.65 | 47 |
| 12.55 | 22 |
| 13.20 | 18 |
| 14.70 | 18 |
| 15.60 | 50 |
| 17.45 | 26 |
| 19.95 | 99 |
| 20.65 | 73 |
| 22.30 | 100 |
| 23.65 | 40 |
| 25.10 | 34 |
| 25.55 | 36 |
| 26.30 | 27 |
| 33.85 | 13. |

5. The crystalline Form I according to claim 1, which shows a FT-IR spectrum in KBR with the following main peaks:

| Frequency (cm−1) | Intensity (% T) |
|---|---|
| 3253.2 | 56 |
| 3031.2 | 60 |
| 2951.3 | 55 |
| 2918.9 | 36 |
| 2848.9 | 41 |
| 1668.9 | 43 |
| 1600.4 | 38 |
| 1561.1 | 41 |
| 1469.7 | 47 |
| 1445.8 | 60 |
| 1418.1 | 56 |
| 1390.3 | 44 |
| 1324.3 | 59 |
| 1265.8 | 55 |
| 1197.4 | 70 |
| 1138.5 | 77 |
| 1089.0 | 76 |
| 1070.4 | 75 |
| 969.6 | 70 |
| 933.7 | 58 |
| 901.5 | 77 |
| 870.9 | 76 |
| 808.2 | 80 |
| 720.0 | 55 |
| 501.0 | 76. |

6. A process for the preparation of the crystalline Form I according to claim 1, comprising the following steps: a) adding under stirring tetrabutylammonium chloride and tetradecylisocyanate to a solution of (R)-aminocarnitine in methanol, thus producing a first suspension in organic solvent; b) filtering the first suspension and concentrating the organic solvent under vacuum, thus obtaining a viscous oil; c) adding acetonitrile to the viscous oil and stirring overnight to give a solid; d) separating the solid by filtration, washing with acetonitrile, dissolving in water and filtering, thus obtaining a clear solution; e) dropping the clear solution into a container containing acetonitrile under stirring, thus obtaining a second suspension; f) allowing the second suspension to sediment, thus obtaining a white solid product at the bottom of the container; and g) isolating the white solid from the solvent.

* * * * *

UNITED STATES PATENT AND TRADEMARK OFFICE
CERTIFICATE OF CORRECTION

PATENT NO.        : 8,598,384 B2
APPLICATION NO. : 12/672099
DATED             : December 3, 2013
INVENTOR(S)       : Cabri et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 967 days.

Signed and Sealed this
Twenty-second Day of September, 2015

Michelle K. Lee
*Director of the United States Patent and Trademark Office*